US012605457B2

(12) United States Patent
Xia et al.

(10) Patent No.: US 12,605,457 B2
(45) Date of Patent: Apr. 21, 2026

(54) MODIFIED EGFR ANTIBODY WITH REDUCED AFFINITY, DRUG CONJUGATE, AND USE THEREOF

(71) Applicant: BLISS BIOPHARMACEUTICAL (HANGZHOU) CO., LTD., Zhejiang (CN)

(72) Inventors: Bing Xia, Zhejiang (CN); Yuhong Zhou, Zhejiang (CN); Ziping Wei, Zhejiang (CN); Lixia Cao, Zhejiang (CN); Fangdun Jiang, Zhejiang (CN)

(73) Assignee: BLISS BIOPHARMACEUTICAL (HANGZHOU) CO., LTD., Hangzhou (CN)

( * ) Notice: Subject to any disclaimer, the term of this patent is extended or adjusted under 35 U.S.C. 154(b) by 522 days.

(21) Appl. No.: 18/253,681

(22) PCT Filed: Nov. 19, 2021

(86) PCT No.: PCT/CN2021/131780
§ 371 (c)(1),
(2) Date: May 19, 2023

(87) PCT Pub. No.: WO2022/105878
PCT Pub. Date: May 27, 2022

(65) Prior Publication Data
US 2024/0009318 A1      Jan. 11, 2024

Related U.S. Application Data

(63) Continuation-in-part of application No. PCT/CN2020/130417, filed on Nov. 20, 2020, and a continuation-in-part of application No. PCT/CN2020/130409, filed on Nov. 20, 2020.

(30) Foreign Application Priority Data

Nov. 20, 2020    (WO) ................ PCT/CN2020/130409
Nov. 20, 2020    (WO) ................ PCT/CN2020/130417

(51) Int. Cl.
*A61P 35/00*        (2006.01)
*A61K 31/357*       (2006.01)
*A61K 38/04*        (2006.01)
*A61K 47/68*        (2017.01)
*C07K 16/28*        (2006.01)

(52) U.S. Cl.
CPC ...... *A61K 47/68031* (2023.08); *A61K 31/357* (2013.01); *A61K 38/04* (2013.01); *A61K 47/6849* (2017.08); *A61K 47/6889* (2017.08); *A61P 35/00* (2018.01); *C07K 16/2863* (2013.01)

(58) Field of Classification Search
None
See application file for complete search history.

(56) References Cited

U.S. PATENT DOCUMENTS

| | | | |
|---|---|---|---|
| 2002/0173629 A1* | 11/2002 | Jakobovits | ......... C07K 16/2863 530/388.22 |
| 2017/0335281 A1 | 11/2017 | Loew et al. | |
| 2020/0172879 A1 | 6/2020 | Suri et al. | |

FOREIGN PATENT DOCUMENTS

| | | | |
|---|---|---|---|
| CN | 102971342 A | 3/2013 | |
| CN | 103619881 A | 3/2014 | |
| CN | 103764170 A | 4/2014 | |
| CN | 108025084 A | 5/2018 | |
| CN | 111939267 A | 11/2020 | |
| JP | 2016523867 A | 8/2016 | |
| WO | WO-9850433 A2 * | 11/1998 | .............. A61P 35/00 |
| WO | 2012100346 A1 | 8/2012 | |

OTHER PUBLICATIONS

International Search Report on PCT/CN2021/131780.
Sickmier, EA et al., Plos One, vol. 11, No. 9, Sep. 22, 2016, 1-11.
Japan Patent Office search report on JP2023530648.
Kwan, WO et al. Oncotarget, vol. 9, No. 71, 33446-33458, 2018.
Liu, XJ et al. Cancer Res. vol. 75, No. 17, 3596-3607, 2015.
Caruso, HG et al. Cancer Res. vol. 75, No. 17, 3505-3518, 2015.
Supplementary Partial European Search Report on EP21894025.

* cited by examiner

*Primary Examiner* — Julie Wu
*Assistant Examiner* — Amy M. Chattin
(74) *Attorney, Agent, or Firm* — Yong Chen; Lin Sun-Hoffman; Liu Chen & Hoffman LLP

(57) ABSTRACT

The present invention provides isolated antibodies that bind to the human EGFR protein, and ADCs of the antibodies. Pharmaceutical compositions including the antibodies and ADCs, and methods of treating cancer are also provided.

19 Claims, 5 Drawing Sheets

Specification includes a Sequence Listing.

| Sample | Purity (%) | Quantity (μg/μL) |
|--------|-----------|------------------|
| BB0500-2f | 98.63 | 75.6 |
| BB0500-2g | 99.02 | 82.8 |
| BB0500-2fg | 98.36 | 94.7 |
| BB0500-2gf | 98.60 | 61.2 |

SEQUENCE LISTING

<160> NUMBER OF SEQ ID NOS: 23

<210> SEQ ID NO 1
<211> LENGTH: 119
<212> TYPE: PRT
<213> ORGANISM: Artificial Sequence
<220> FEATURE:
<223> OTHER INFORMATION: VH of BB0500-2f1, BB0500-2f, BB0500-2n and
     BB0500-2fg

<400> SEQUENCE: 1

Gln Val Gln Leu Gln Glu Ser Gly Pro Gly Leu Val Lys Pro Ser Glu
1             5                 10                15

Thr Leu Ser Leu Thr Cys Thr Val Ser Gly Gly Ser Val Ser Ser Gly

-continued

```
                20              25              30

Asp Tyr Tyr Trp Thr Trp Ile Arg Gln Ser Pro Gly Lys Gly Leu Glu
        35              40              45

Trp Ile Gly His Ile Tyr Tyr Ser Gly Asn Ala Asn Tyr Asn Pro Ser
    50              55              60

Leu Lys Ser Arg Leu Thr Ile Ser Ile Asp Thr Ser Lys Thr Gln Phe
65              70              75              80

Ser Leu Lys Leu Ser Ser Val Thr Ala Ala Asp Thr Ala Ile Tyr Tyr
                85              90              95

Cys Val Arg Asp Arg Val Thr Gly Ala Phe Asp Ile Trp Gly Gln Gly
                100             105             110

Thr Met Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: VL of BB0500-2f1 and BB0500-2g1

<400> SEQUENCE: 2

Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
                20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Phe Cys Gln His Phe Asp His Leu Pro Leu
                85              90              95

Ala Phe Gly Gly Gly Thr Lys Val Glu Ile Lys
            100             105

<210> SEQ ID NO 3
<211> LENGTH: 119
<212> TYPE: PRT
<213> ORGANISM: Artificial Sequence
<220> FEATURE:
<223> OTHER INFORMATION: VH of BB0500-2f2 and BB0500-2g2

<400> SEQUENCE: 3

Gln Val Gln Leu Gln Glu Ser Gly Pro Gly Leu Val Lys Pro Ser Glu
1               5               10              15

Thr Leu Ser Leu Thr Cys Thr Val Ser Gly Gly Ser Val Ser Ser Gly
            20              25              30

Asp Tyr Tyr Trp Thr Trp Ile Arg Gln Ser Pro Gly Lys Gly Leu Glu
        35              40              45

Trp Ile Gly His Ile Tyr Tyr Ser Gly Asn Thr Asn Tyr Asn Pro Ser
    50              55              60

Leu Lys Ser Arg Leu Thr Ile Ser Ile Asp Thr Ser Lys Thr Gln Phe
65              70              75              80

Ser Leu Lys Leu Ser Ser Val Thr Ala Ala Asp Thr Ala Ile Tyr Tyr
                85              90              95
```

```
Cys Val Arg Asp Arg Val Thr Gly Ala Phe Asp Ile Trp Gly Gln Gly
        100                 105                 110

Thr Met Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: VL of BB0500-2f2, BB0500-2f, BB0500-2n and
      BB0500-2gf

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 5
<211> LENGTH: 119
<212> TYPE: PRT
<213> ORGANISM: Artificial Sequence
<220> FEATURE:
<223> OTHER INFORMATION: VH of BB0500-2g1, BB0500-2g, and BB0500-2gf

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Ala Gly Ala Phe Asp Ile Trp Gly Gln Gly
            100                 105                 110

Thr Met Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: VL of BB0500-2g2, BB0500-2g, and BB0500-2fg
```

-continued

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ala
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
                100                 105

<210> SEQ ID NO 7
<211> LENGTH: 450
<212> TYPE: PRT
<213> ORGANISM: Artificial Sequence
<220> FEATURE:
<223> OTHER INFORMATION: BB0500-2f1/2f/2fg heavy chain

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Ala Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
                100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Pro Lys Ser Asp Lys Cys
            210                 215                 220

Thr His Thr Val Glu Cys Pro Pro Cys Pro Ala Pro Pro Val Ala Gly
225                 230                 235                 240

```
Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Gln Phe Asn Trp Tyr Val Asp Gly Val Glu Val His
            275             280             285

Asn Ala Lys Thr Lys Pro Arg Glu Glu Gln Phe Asn Ser Thr Phe Arg
    290             295             300

Val Val Ser Val Leu Thr Val Val His Gln Asp Trp Leu Asn Gly Lys
305             310             315             320

Glu Tyr Lys Cys Lys Val Ser Asn Lys Gly Leu Pro Ala Pro Ile Glu
            325             330             335

Lys Thr Ile Ser Lys Thr Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ser Val Glu Trp
    370             375             380

Glu Ser Asn Gly Gln Pro Glu Asn Asn Tyr Lys Thr Thr Pro Pro Met
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

<210> SEQ ID NO 8
<211> LENGTH: 214
<212> TYPE: PRT
<213> ORGANISM: Artificial Sequence
<220> FEATURE:
<223> OTHER INFORMATION: BB0500-2f1/2g1 light chain

<400> SEQUENCE: 8

```
Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
            20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Phe Cys Gln His Phe Asp His Leu Pro Leu
            85              90              95

Ala Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 9
<211> LENGTH: 451
<212> TYPE: PRT
<213> ORGANISM: Artificial Sequence
<220> FEATURE:
<223> OTHER INFORMATION: BB0500-2f2/2g2 heavy chain

<400> SEQUENCE: 9

Gln Val Gln Leu Gln Glu Ser Gly Pro Gly Leu Val Lys Pro Ser Glu
1                   5                   10                  15

Thr Leu Ser Leu Thr Cys Thr Val Ser Gly Gly Ser Val Ser Ser Gly
                20                  25                  30

Asp Tyr Tyr Trp Thr Trp Ile Arg Gln Ser Pro Gly Lys Gly Leu Glu
            35                  40                  45

Trp Ile Gly His Ile Tyr Tyr Ser Gly Asn Thr Asn Tyr Asn Pro Ser
        50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Pro Lys Ser Asp Cys Lys
        210                 215                 220

Thr His Thr Val Glu Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

-continued

```
His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: BB0500-2f2/2f/2gf/2n light chain

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 451
<212> TYPE: PRT
<213> ORGANISM: Artificial Sequence
<220> FEATURE:
<223> OTHER INFORMATION: BB0500-2g1/2g/2gf heavy chain

<400> SEQUENCE: 11

Gln Val Gln Leu Gln Glu Ser Gly Pro Gly Leu Val Lys Pro Ser Glu
1                 5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
            85                  90                  95

Cys Val Arg Asp Arg Val Ala Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Pro Pro Lys Ser Cys Asp
        210                 215                 220

Lys Thr His Thr Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
            325                 330                 335
```

```
Glu Lys Thr Ile Ser Lys Thr Lys Gly Gln Pro Arg Glu Pro Gln Val
            340             345             350

Tyr Thr Leu Pro Pro Ser Arg Glu Glu Met Thr Lys Asn Gln Val Ser
            355             360             365

Leu Thr Cys Leu Val Lys Gly Phe Tyr Pro Ser Asp Ile Ser Val Glu
            370             375             380

Trp Glu Ser Asn Gly Gln Pro Glu Asn Asn Tyr Lys Thr Thr Pro Pro
385             390             395             400

Met Leu Asp Ser Asp Gly Ser Phe Phe Leu Tyr Ser Lys Leu Thr Val
            405             410             415

Asp Lys Ser Arg Trp Gln Gln Gly Asn Val Phe Ser Cys Ser Val Met
            420             425             430

His Glu Ala Leu His Asn His Tyr Thr Gln Lys Ser Leu Ser Leu Ser
            435             440             445

Pro Gly Lys
    450
```

```
<210> SEQ ID NO 12
<211> LENGTH: 214
<212> TYPE: PRT
<213> ORGANISM: Artificial Sequence
<220> FEATURE:
<223> OTHER INFORMATION: BB0500-2g2/2g/2fg light chain

<400> SEQUENCE: 12
```

```
Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Ala
            20              25              30

Leu Asn Trp Tyr Gln Gln Lys Pro Gly Lys Ala Pro Lys Leu Leu Ile
            35              40              45

Tyr Asp Ala Ser Asn Leu Glu Thr Gly Val Pro Ser Arg Phe Ser Gly
            50              55              60

Ser Gly Ser Gly Thr Asp Phe Thr Phe Thr Ile Ser Ser Leu Gln Pro
65              70              75              80

Glu Asp Ile Ala Thr Tyr Phe Cys Gln His Phe Asp His Leu Pro Leu
            85              90              95

Ala Phe Gly Gly Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210
```

```
<210> SEQ ID NO 13
<211> LENGTH: 452
```

US 12,605,457 B2

33

34

-continued

<212> TYPE: PRT
<213> ORGANISM: Artificial Sequence
<220> FEATURE:
<223> OTHER INFORMATION: BB0500-2n heavy chain

<400> SEQUENCE: 13

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Ala Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Pro Pro Lys Ser Asp Cys
    210                 215                 220

Lys Thr His Thr Val Glu Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380
```

-continued

```
Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
        420             425             430

Met His Glu Ala Leu His Asn His Tyr Thr Gln Lys Ser Leu Ser Leu
        435             440             445

Ser Pro Gly Lys
    450

<210> SEQ ID NO 14
<211> LENGTH: 9
<212> TYPE: PRT
<213> ORGANISM: Artificial Sequence
<220> FEATURE:
<223> OTHER INFORMATION: VH CDR1 of
      BB0500-2f1/2f2/2g1/2g2/2f/2g/2fg/2gf/2n, wt

<400> SEQUENCE: 14

Gly Gly Ser Val Ser Ser Gly Asp Tyr
1               5

<210> SEQ ID NO 15
<211> LENGTH: 6
<212> TYPE: PRT
<213> ORGANISM: Artificial Sequence
<220> FEATURE:
<223> OTHER INFORMATION: VH CDR2 of BB0500-2f/2f1/2fg/2n, with T59A
      mutation

<400> SEQUENCE: 15

Tyr Tyr Ser Gly Asn Ala
1               5

<210> SEQ ID NO 16
<211> LENGTH: 6
<212> TYPE: PRT
<213> ORGANISM: Artificial Sequence
<220> FEATURE:
<223> OTHER INFORMATION: VH CDR2 of BB0500-2f2/2g1/2g2/2g/2gf, wt

<400> SEQUENCE: 16

Tyr Tyr Ser Gly Asn Thr
1               5

<210> SEQ ID NO 17
<211> LENGTH: 9
<212> TYPE: PRT
<213> ORGANISM: Artificial Sequence
<220> FEATURE:
<223> OTHER INFORMATION: VH CDR3 of BB0500-2g/2g1/2gf, with T103A
      mutation

<400> SEQUENCE: 17

Asp Arg Val Ala Gly Ala Phe Asp Ile
1               5

<210> SEQ ID NO 18
<211> LENGTH: 9
<212> TYPE: PRT
<213> ORGANISM: Artificial Sequence
<220> FEATURE:
<223> OTHER INFORMATION: VH CDR3 of BB0500-2f1/2f2/2g2/2f/2fg/2n, wt

<400> SEQUENCE: 18
```

Asp Arg Val Thr Gly Ala Phe Asp Ile
1               5

<210> SEQ ID NO 19
<211> LENGTH: 11
<212> TYPE: PRT
<213> ORGANISM: Artificial Sequence
<220> FEATURE:
<223> OTHER INFORMATION: VL CDR1 of BB0500-2g2/2g/2fg, with Y32A
      mutation

<400> SEQUENCE: 19

Gln Ala Ser Gln Asp Ile Ser Asn Ala Leu Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: VL CDR1 of BB0500-2f1/2f2/2g1/2f/2gf/2n, wt

<400> SEQUENCE: 20

Gln Ala Ser Gln Asp Ile Ser Asn Tyr Leu Asn
1               5                   10

<210> SEQ ID NO 21
<211> LENGTH: 7
<212> TYPE: PRT
<213> ORGANISM: Artificial Sequence
<220> FEATURE:
<223> OTHER INFORMATION: VL CDR2 of BB0500-2f2/2f/2gf/2n, with D50A
      mutation

<400> SEQUENCE: 21

Ala Ala Ser Asn Leu Glu Thr
1               5

<210> SEQ ID NO 22
<211> LENGTH: 7
<212> TYPE: PRT
<213> ORGANISM: Artificial Sequence
<220> FEATURE:
<223> OTHER INFORMATION: VL CDR2 of BB0500-2f1/2g1/2g2/2g/2fg, wt

<400> SEQUENCE: 22

Asp Ala Ser Asn Leu Glu Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL CDR3 of
      BB0500-2f1/2f2/2g1/2g2/2f/2g/2fg/2gf/2n, wt

<400> SEQUENCE: 23

Gln His Phe Asp His Leu Pro Leu Ala
1               5

MODIFIED EGFR ANTIBODY WITH REDUCED AFFINITY, DRUG CONJUGATE, AND USE THEREOF

CROSS REFERENCE TO RELATED APPLICATIONS

This application claims priority to International Application No. PCT/CN2020/130409 filed Nov. 20, 2020, and to International Application No. PCT/CN2020/130417 filed Nov. 20, 2020, the disclosures of both of which are incorporated by reference herein in their entireties.

BACKGROUND

Antibodies are key immune molecules acting against foreign pathogens. The development of monoclonal antibody (mAb) technology resulted in widespread use of monoclonal antibodies in research, diagnosis and treatment of diseases. The therapeutic use of first-generation mAb (mostly monospecific, bivalent mAb) achieved success in the treatment of a variety of diseases, including cancer, autoimmune, and infectious diseases. However, many diseases, such as solid tumors, have been shown to be quite resistant to antibody-based therapies.

Antibody Drug Conjugates (ADCs) are mAbs chemically linked to active drugs, and therefore, have both the specific targeting of mAbs and the cancer-killing ability of cytotoxic drugs. The ability to select specific mAbs-drug combination and advances in the linking the mAbs and drugs provides new possibilities to target cancers while minimizing exposure of healthy tissue. By 2019, a total of seven ADCs have been approved by the FDA, including: ado-trastuzumab emtansine (Kadcyla™), brentuximab vedotin (Adcetris™), inotuzumab ozogamicin (Besponsa™), gemtuzumab ozogamicin (Mylotarg™), polatuzumab vedotin-piiq (Polivy™), Enfortumab vedotin (Padcev™), and Trastuzumab deruxtecan (Enhertu™). All of them involve conjugation of a cytotoxic drug with a bivalent mAb. In addition to the seven ADC drugs that have been approved for marketing, a large number of ADCs are currently under clinical development.

The epidermal growth factor receptor (EGFR, also known as HER1 or c-erbB-1) is a 170 kDa transmembrane glycoprotein and a member of the tyrosine kinase family of cell surface receptors[1, 2]. EGFR is abnormally activated in many epithelial tumors, including those in non-small cell lung cancer, breast cancer, colorectal cancer, head and neck cancers, and glioblastoma[3-8]. Abnormal activation of EGFR can arise from overexpression of the receptor, gene amplification, activating mutations, overexpression of receptor ligands, and/or loss of regulators of EGFR activity.

Interruption of EGFR signaling, either by blocking EGFR binding sites on the extracellular domain of the receptor or by inhibiting intracellular tyrosine kinase activity, can inhibit the growth of EGFR-expressing tumors and improve the patient's condition[9-11]. Anti-EGFR antibodies exert antitumor effects by binding the receptor at the cell surface to interfere with ligand binding, which leads to the inhibition of its downstream signaling pathway[12-13]. Several ligand-blocking antibodies for EGFR, including cetuximab, nimotuzumab, panitumumab, and necitumumab, have been approved for the treatment of various types of cancers[13]. Panitumumab is a clinically proven antibody that targeted EGFR potently and specifically. However, clinical response to Panitumumab is often accompanied by significant toxicities due to normal tissue expression[14]. Also, while the extremely high affinity ($KD=10^{-11}M$) of Panitumumab made it a potent blocker of EGFR/EGF engagement, it made Panitumumab undesirable for ADC construction because of the potentially further compounded side effects with the cytotoxic drug.

SUMMARY OF THE INVENTION

In one aspect of the present disclosure, an isolated antibody is provided, which comprises (a1) a heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b1) a light chain variable domain comprising a CDR1 region, a CDR2 region, and a CDR3 region comprising the amino acid sequences of SEQ ID NO: 20, SEQ ID NO: 21, and SEQ ID NO: 23, respectively. Another isolated antibody is provided, which comprises: (a2) a heavy chain variable domain comprising a CDR1 region, a CDR2 region, and a CDR3 region comprising the amino acid sequences of SEQ ID NO: 14, SEQ ID NO: 16, and SEQ ID NO: 17, respectively, and (b2) a light chain variable domain comprising a CDR1 region, a CDR2 region, and a CDR3 region comprising the amino acid sequences of SEQ ID NO: 19, SEQ ID NO: 22, and SEQ ID NO: 23, respectively. Another isolated antibody is provided, which comprises: (a3) heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b3) a light chain variable domain comprising a CDR1 region, a CDR2 region, and a CDR3 region comprising the amino acid sequences of SEQ ID NO: 20, SEQ ID NO: 22, and SEQ ID NO: 23, respectively. Another isolated antibody is provided, which comprises: (a4) a heavy chain variable domain comprising a CDR1 region, a CDR2 region, and a CDR3 region comprising the amino acid sequences of SEQ ID NO: 14, SEQ ID NO: 16, and SEQ ID NO: 18, respectively, and (b4) a light chain variable domain comprising a CDR1 region, a CDR2 region, and a CDR3 region comprising the amino acid sequences of SEQ ID NO: 20, SEQ ID NO: 21, and SEQ ID NO: 23, respectively. These antibodies specifically bind with human EGFR protein. In some embodiments, the antibody binds with human EGFR with a KD of in the range of from about $1\times10^{-9}M$ to about $5\times10^{-8}M$.

In one aspect of the present disclosure, an isolated antibody is provided, which comprises: (a) a heavy chain having a variable domain comprising the amino acid sequence of SEQ ID NO: 1, and a light chain having a variable domain comprising the amino acid sequence of SEQ ID NO: 4; or (b) a heavy chain having a variable domain comprising the amino acid sequence of SEQ ID NO: 5, and a light chain having a variable domain comprising the amino acid sequence of SEQ ID NO: 6; or (c) a heavy chain having a variable domain comprising the amino acid sequence of SEQ ID NO: 1, and a light chain having a variable domain comprising the amino acid sequence of SEQ ID NO: 2; or (d) a heavy chain having a variable domain comprising the amino acid sequence of SEQ ID NO: 3, and a light chain having a variable domain comprising the amino acid sequence of SEQ ID NO: 4.

In another aspect of the present disclosure, an isolated antibody is provided, which comprises: (a) a heavy chain comprising the amino acid sequence of SEQ ID NO: 7, and a light chain comprising the amino acid sequence of SEQ ID NO: 10; or (b) a heavy chain comprising the amino acid sequence of SEQ ID NO: 13, and a light chain comprising the amino acid sequence of SEQ ID NO: 10; or (c) a heavy chain comprising the amino acid sequence of SEQ ID NO: 11, and a light chain comprising the amino acid sequence of SEQ ID NO: 12; or (d) a heavy chain comprising the amino acid sequence of SEQ ID NO: 7, and a light chain comprising the amino acid sequence of SEQ ID NO: 8; or (e) a heavy chain comprising the amino acid sequence of SEQ ID NO: 9, and a light chain comprising the amino acid sequence of SEQ ID NO: 10.

The antibody of the present application can be monoclonal antibody. In some embodiments, the antibody of the present disclosure can be deemed as the antibody Panitumumab, which is the first fully human monoclonal antibody directed against the EGFR, being mutated at one amino acid on its heavy chain and one amino acid on its light chain. The heavy chain mutation can be T103A while the light chain mutation is Y32A, or the heavy chain mutation can be T59A while the light chain mutation is D50A.

In further aspects, a nucleic acid molecule encoding the antibody described herein, an expression vector containing the nucleic acid molecule, and a host cell containing the expression vector are also provided.

In yet a further aspect, the present disclosure provides an antibody-drug conjugate (ADC) or a pharmaceutically acceptable salt thereof that comprises the antibody described herein conjugated to a cytotoxic drug molecule by a chemical linker. In some embodiments, the cytotoxic drug can be selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, irinotecan (SN38), exatecan, and nanoparticles.

The chemical linker linking the antibody portion and the cytotoxic drug can be cleavable or non-cleavable. In some embodiments, the linker comprises a PEGn spacer where n is between 1 and 20 (i.e., having 1 to 20 repeat units ($CH_2CH_2O$)). In some embodiments, the chemical linker further comprises a linker segment connected to the PEGn spacer. In some embodiments, the chemical linker comprises a linker segment but does not comprise a PEGn spacer. In some embodiments, the linker segment can be selected from the group consisting of 6-maleimidocaproyl (MC), maleimidopropionyl (MP), valine-citrulline (Val-Cit), alanine-phenylalanine (ala-phe), p-aminobenzyloxycarbonyl (PAB), 6-maleimidocaproyl-valine-citrulline-p-aminobenzyloxycarbonyl (MC-Val-Cit-PAB), Mal-PEG$_n$-Val-Cit-PAB (n=1-20), Phe-Lys(Fmoc)-PAB, Aloc-D-Ala-Phe-Lys(Aloc)-PAB-PNP, Boc-Phe-(Alloc)Lys-PAB-PNP, and perfluorophenyl 3-(pyridine-2-yldisulfanyl) propanoate, or combinations thereof.

In further aspect, the present disclosure provides a pharmaceutical composition comprising one or more antibodies, ADCs or the pharmaceutically acceptable salts thereof, of the present invention, together with a pharmaceutically acceptable carrier.

In a further aspect, the present disclosure provides a method of treating disease such as cancer in a human subject, comprising administering to the subject a therapeutically effective amount of the pharmaceutical composition described herein. The cancer can include non-small cell lung cancer, epidermoid carcinoma, breast cancer, colorectal cancer, ovarian cancer, cervical cancer, bladder cancer, oesophageal cancer, head and neck cancers, -glioblastoma, nasopharyngeal cancer.

DETAILED DESCRIPTION

Figures 1, 2:
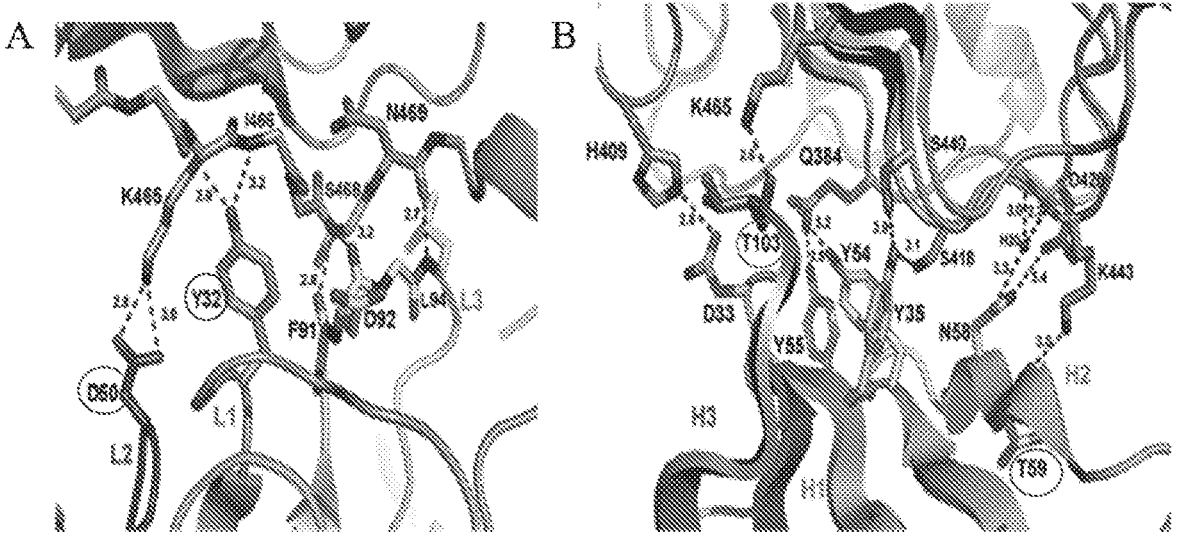
FIG. 1 shows schematic diagrams of interactions between paratope surfaces of EGFR protein and CDRs of panitumumab. (A) Panitumumab light chain CDR interactions with the final β-strand of EGFR domain III. EGFR on top interactions with L1, L2 and L3 CDRs of the panitumumab on the bottom. (B) Panitumumab heavy chain CDR interactions with the β-sheet surface of EGFR domain III that binds EGFR. EGFR is shown on top with H1, H2, and H3 CDR regions. Amino acids subject to mutation are circled.
FIG. 2 shows characterization of antibodies according to some embodiments of the present invention. (a) purity and yields of certain antibodies produced in HEK293 cells; (b) SDS-PAGE plots of reducing (R) and Non-Reducing (NR) antibodies; (c) SEC-HPLC analysis of purified antibodies.

The present disclosure provides antibodies based on modification of the amino acid sequences of panitumumab. Without losing the binding specificity to EGFR, the modified (or mutant) antibody has reduced affinity to the antigen, and has reduced toxicities on normal tissues. ADCs based on these antibodies are also provided. According to some embodiments, compared with the ADC made from the parent wild-type panitumumab and a same toxin, ADCs made of the mutant antibodies retain comparable potency in terms of killing EGFR high-expressing tumor cells, while having significantly reduced potencies to EGFR low-expressing cells. Therefore, treatment with an ADC made of such mutant antibody can have a better therapeutic window with less on-target-off-tumor toxicities to EGFR low-expressing normal skin tissues that was associated with Panitumumab treatment.

The term "monoclonal antibody" as used herein refer to a preparation of antibody molecules of single molecular composition.

An antibody or molecule that "specifically binds to human EGFR" refers to an antibody or polypeptide molecule that binds to human EGFR protein but does not substantially bind to proteins that are not human EGFR proteins.

In one aspect of the present disclosure, an isolated antibody is provided, which comprises (a1) a heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b1) a light chain variable domain comprising a CDR1 region, a CDR2 region, and a CDR3 region comprising the amino acid sequences of SEQ ID NO: 20, SEQ ID NO: 21, and SEQ ID NO: 23, respectively. Another isolated antibody is provided, which comprises: (b1) a heavy chain variable domain comprising a CDR1 region, a CDR2 region, and a CDR3 region comprising the amino acid sequences of SEQ ID NO: 14, SEQ ID NO: 16, and SEQ ID NO: 17, respectively, and (b2) a light chain variable domain comprising a CDR1 region, a CDR2 region, and a CDR3 region comprising the amino acid sequences of SEQ ID NO: 19, SEQ ID NO: 22, and SEQ ID NO: 23, respectively. Another isolated antibody is provided, which comprises: (a3) heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b3) a light chain variable domain comprising a CDR1 region, a CDR2 region, and a CDR3 region comprising the amino acid sequences of SEQ ID NO: 20, SEQ ID NO: 22, and SEQ ID NO: 23, respectively. Another isolated antibody is provided, which comprises: (a4) a heavy chain variable domain comprising a CDR1 region, a CDR2 region, and a CDR3 region comprising the amino acid sequences of SEQ ID NO: 14, SEQ ID NO: 16, and SEQ ID NO: 18, respectively, and (b4) a light chain variable domain comprising a CDR1 region, a CDR2 region, and a CDR3 region comprising the amino acid sequences of SEQ ID NO: 20, SEQ ID NO: 21, and SEQ ID NO: 23, respectively. These antibodies specifically binds with human EGFR protein. In some embodiments, the antibody binds with human EGFR with a KD of in the range of from about $1 \times 10^{-9}$ M to about $5 \times 10^{-8}$ M.

In one aspect of the present disclosure, an isolated antibody is provided, which comprises: (a) a heavy chain having a variable domain comprising the amino acid sequence of SEQ ID NO: 1, and a light chain having a variable domain comprising the amino acid sequence of SEQ ID NO: 4; or (b) a heavy chain having a variable domain comprising the amino acid sequence of SEQ ID NO: 5, and a light chain having a variable domain comprising the amino acid sequence of SEQ ID NO: 6; or (c) a heavy chain having a variable domain comprising the amino acid sequence of SEQ ID NO: 1, and a light chain having a variable domain comprising the amino acid sequence of SEQ ID NO: 2; or (d) a heavy chain having a variable domain comprising the amino acid sequence of SEQ ID NO: 3, and a light chain having a variable domain comprising the amino acid sequence of SEQ ID NO: 4.

In another aspect of the present disclosure, an isolated antibody is provided, which comprises: (a) a heavy chain comprising the amino acid sequence of SEQ ID NO: 7, and a light chain comprising the amino acid sequence of SEQ ID NO: 10; or (b) a heavy chain comprising the amino acid sequence of SEQ ID NO: 13, and a light chain comprising the amino acid sequence of SEQ ID NO: 10; or (c) a heavy chain comprising the amino acid sequence of SEQ ID NO: 11, and a light chain comprising the amino acid sequence of SEQ ID NO: 12; or (d) a heavy chain comprising the amino acid sequence of SEQ ID NO: 7, and a light chain comprising the amino acid sequence of SEQ ID NO: 8; or (e) a heavy chain comprising the amino acid sequence of SEQ ID NO: 9, and a light chain comprising the amino acid sequence of SEQ ID NO: 10.

DNA encoding an amino acid sequence variant of a starting polypeptide can prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide.

Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant engineered antibodies.

In yet a further aspect, the present disclosure provides a nucleic acid molecule encoding the antibody or antigen-binding portion thereof of any of the antibody described herein. A host cell (e.g., a CHO cell, a human embryonic kidney cell, a lymphocytic cell, or microorganisms, such as *E. coli*, and fungi, such as yeast) containing an expression vector containing the nucleic acid molecule, can be used to produce antibodies of the present disclosure, preferably monoclonal antibodies. In one embodiment, DNA encoding partial or full-length antibody of the present disclosure can be obtained by standard molecular biology techniques is inserted into one or more expression vectors such that the genes are operatively linked to transcriptional and translational regulatory sequences. The term "operatively linked" is intended to mean that an antibody gene is ligated into a vector such that transcriptional and translational control sequences within the vector serve their intended function of regulating the transcription and translation of the antibody gene. The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody encoding DNA can be inserted into the expression vector. The recombinant expression vector can encode a signal peptide that facilitates secretion of the antibody chain from a host cell. The antibody encoding DNA can be cloned into the vector such that the signal peptide is linked in-frame to the amino terminus of the antibody encoding DNA. The signal peptide can be an immunoglobulin signal peptide or a heterologous signal peptide (i.e., a signal peptide from a non-immunoglobulin protein).

In a further aspect, the present disclosure provides an antibody-drug conjugate (ADC) or a pharmaceutically acceptable salt thereof that comprises the antibody described herein conjugated to a cytotoxic drug molecule by a chemical linker. In some embodiments, the cytotoxic drug can be selected from the group consisting of monomethyl auristatin E (MMAE), monomethyl auristatin F (MMAF), auristatin E, auristatin F, maytansine DM1 and DM4, maytansinol, sandramycin, pyrrolobenzodiazepine, pyrrolobenzodiazepine dimer, anthracyclines, calicheamicin, dolastatin 10, duocarmycin, doxorubicin, thailanstatin A, uncialamycin, amanitins, ricin, diphtheria toxin, eribulin, $^{131}$I, interleukins, tumor necrosis factors, chemokines, irinotecan (SN38), exatecan, and nanoparticles.

The chemical linker linking the antibody portion and the cytotoxic drug can be cleavable or non-cleavable. In some embodiments, the linker comprises a PEGn spacer where n is between 1 and 20 (i.e., having 1 to 20 repeat units $(CH_2CH_2O)$). In some embodiments, the chemical linker further comprises a linker segment connected to the PEGn spacer. In some embodiments, the chemical linker comprises a linker segment but does not comprise a PEGn spacer. In some embodiments, the linker segment can be selected from the group consisting of 6-maleimidocaproyl (MC), maleimidopropionyl (MP), valine-citrulline (Val-Cit), alanine-phenylalanine (ala-phe), p-aminobenzyloxycarbonyl (PAB), 6-maleimidocaproyl-valine-citrulline-p-aminobenzyloxycarbonyl (MC-Val-Cir-PAB), Mal-PEG$_n$-Val-Cit-PAB (n=1-20), Phe-Lys(Fmoc)-PAB, Aloc-D-Ala-Phe-Lys(Aloc)-PAB-PNP, Boc-Phe-(Alloc)Lys-PAB-PNP, and perfluorophenyl 3-(pyridine-2-yldisulfanyl) propanoate, or combinations thereof.

In further aspect, the present disclosure provides a pharmaceutical composition comprising one or more antibodies, ADCs or the pharmaceutically acceptable salts thereof, of the present invention, together with a pharmaceutically acceptable carrier. As used herein, "pharmaceutically acceptable carrier" includes pharmaceutically acceptable carriers, excipients or stabilizers. These include but are not limited solvents, dispersion media, coatings, antibacterial and antifungal agents, isotonic and absorption delaying agents, surface active agents, thickening or emulsifying agents, solid binders, dispersion or suspension aids, solubilizers, colorants, flavoring agents, coatings, disintegrating agents, lubricants, sweeteners, preservatives, isotonic agents, and the like that are physiologically compatible. The selection of suitable carrier is within the knowledge of an artisan skilled in the art. The composition may comprise one or more additional pharmaceutically active ingredients, such as another antibody, a drug, e.g., a cytotoxic or anti-tumor agent. The pharmaceutical compositions of the invention also can be administered in a combination therapy with, for example, another anti-cancer agent, another anti-inflammatory agent, etc.

The pharmaceutical composition can be suitable for intravenous, intramuscular, subcutaneous, parenteral, epidermal, and other routes of administration. Depending on the route of administration, the active ingredient can be coated with a material or otherwise loaded in a material or structure to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the composition of the invention can be administered via a non-parenteral route, such as a topical, epidermal or mucosal route of administration, e.g., intranasally, orally, vaginally, rectally, sublingually or topically.

In another aspect, the present disclosure provides a method for treating disease such as cancer in a human subject, comprising administering to the subject a therapeutically effective amount of the pharmaceutical composition described herein. The cancer can be one of those cancers associated with increased EGFR expression. For example, the cancer can include non-small cell lung cancer, epidermoid carcinoma, breast cancer, colorectal cancer, ovarian cancer, cervical cancer, bladder cancer, oesophageal cancer, head and neck cancers, glioblastoma and nasopharyngeal cancer.

In the administration of the composition to the subject, dosage regimens can be adjusted to provide the optimum desired response (e.g., a therapeutic response). Single bolus or divided doses can be administered based on the subject, the disease to be treated, etc. Dosage unit form as used herein refers to physically discrete units suited as unitary dosages for the subjects to be treated. Each unit contains a predetermined quantity of active ingredient calculated to produce the desired therapeutic effect in association with the required pharmaceutical carrier. Sustained release formulation can be used in which case less frequent administration is required.

For administration of an antibody or ADC pharmaceutical salts thereof of the present disclosure, the dosage may range from about 0.0001 to 100 mg/kg, and more usually 0.01 to 10 mg/kg, of the body weight of the subject. For example dosages can be 0.3 mg/kg body weight, 1 mg/kg body weight, 3 mg/kg body weight, 5 mg/kg body weight or 10 mg/kg body weight or within the range of 1-10 mg/kg. A suitable treatment regime can be once per week, once every two weeks, once every three weeks, once every four weeks, once a month, etc. Example dosage regimens for an anti-EGFR antibody of the invention can include 1 mg/kg body weight or 3 mg/kg body weight via intravenous administration.

A "therapeutically effective amount" or "therapeutically effective amount" of an antibody or ADC or pharmaceutical salts thereof of the invention preferably results in a decrease in severity of disease symptoms, an increase in frequency and/or duration of disease symptom-free periods, prevention or reduction of likelihood of impairment or disability due to the disease affliction, or inhibition or delaying of the progression of disease. For example, for the treatment of tumor-bearing subjects, a "therapeutically effective amount" of an antibody composition may inhibits tumor growth by at least about 20%, more preferably by at least about 40%, even more preferably by at least about 60%, and still more preferably by at least about 80% relative to untreated subjects.

EXAMPLES

1. Design of Panitumumab Mutant Antibodies with Lower Antigen Affinities.

A high-resolution 3D structure analysis of Panitumumab/EGFR complex revealed that, while L3 CDR commonly make the largest contributions to antigen binding, the L2 CDR makes only a single interaction through a solvent exposed salt bridge between D50 and K465 of EGFR domain III, and the L1 CDR makes another single interaction through a solvent exposed hydrogen bond bridge between Y32 and 1466 of EGFR domain III (FIG. 1A). This is consistent with the general observation that L1/L2 CDR often makes minor binding contribution. On the heavy chain side, while H2 and H3 CDRs account for most of the central buried specific interactions between Panitumumab and EGFR domain III, a H2 CDR hydrogen bonds include the carbonyl of T59 to K443 of EGFR domain III is highly solvent exposed. H3 makes an additional hydrogen bond between the carbonyl of T103 and K465 of EGFR domain III which is also highly solvent exposed (FIG. 1B). The solvent exposed nature of the above interactions prompted the current inventors to hypothesize that substitution of amino acid residues in CDRs L2D50, L1Y32, H2T59 or H3T103 with an amino acid containing a shorter side chain would cause only minor affinity loss, and might cause insignificant disruptions to the antibody/antigen interaction interfaces.

Alanine-scanning techniques were used to make mutants with alanine substitution to each identified amino acid. The mutant antibodies were generated with each of the mutant heavy or light chain pairing with a wild type (of Panitumumab) or mutant light or heavy chain. 8 resulting mutant antibodies (with their VH and VL regions and corresponding SEQ ID NOs shown in the below table) with single or double mutations were subject to EGFR binding measurement.

TABLE 1

| List of mutant antibodies and control antibody | | | | |
| --- | --- | --- | --- | --- |
| | Mutation (or wt) | | SEQ ID NO: | |
| Clone ID | VH | VL | VH | VL |
| BB0500-2f1 | T59A | wt | 1 | 2 |
| BB0500-2f2 | wt | D50A | 3 | 4 |
| BB0500-2g1 | T103A | wt | 5 | 2 |
| BB0500-2g2 | wt | Y32A | 3 | 6 |
| BB0500-2f | T59A | D50A | 1 | 4 |
| BB0500-2g | T103A | Y32A | 5 | 6 |
| BB0500-2fg | T59A | Y32A | 1 | 6 |
| BB0500-2gf | T103A | D50A | 5 | 4 |
| BB0500-2n | T59A | D50A | 1 | 4 |
| BB0500-2d (panitumumab, as control) | wt | wt | | |

For expression of the mutant antibodies, codon optimization and gene synthesis were performed. Specific full-length heavy chain and light chain DNA were each cloned into a separate pcDNA3 plasmid. HEK293 cell transient transfection of the paired plasmids and one-step Protein A purification was used to prepare enough proteins for testing. Antibodies made in this format expressed well with decent yield and could be purified in high purity with one step protein A purification process (FIG. 2a, b, c).

2. Measurement of EGFR Binding Affinities of the Mutant Antibodies ELISA assay was used to exam and compare the EGFR binding capabilities between the mutant antibodies and control wild type (wt) antibody. Mutant antibody samples or control antibodies diluted in 5-fold serial dilutions starting from 10 μg/mL and 8 dilutions total, were coated onto 96-well plates and the plates were incubated at 4° C. overnight. Using HRP-labeled goat anti-human IgG Fc antibody (Sigma, A0170) in 40000 dilution as a detection agent and TMB for colorimetric reaction, the plates read at 450/650 nm for absorbance on Microplate Reader (Molecular Devices, SpectraMax 190) and data analysis was performed using a dose response curve format four parameters logistic model.

Figure 3:
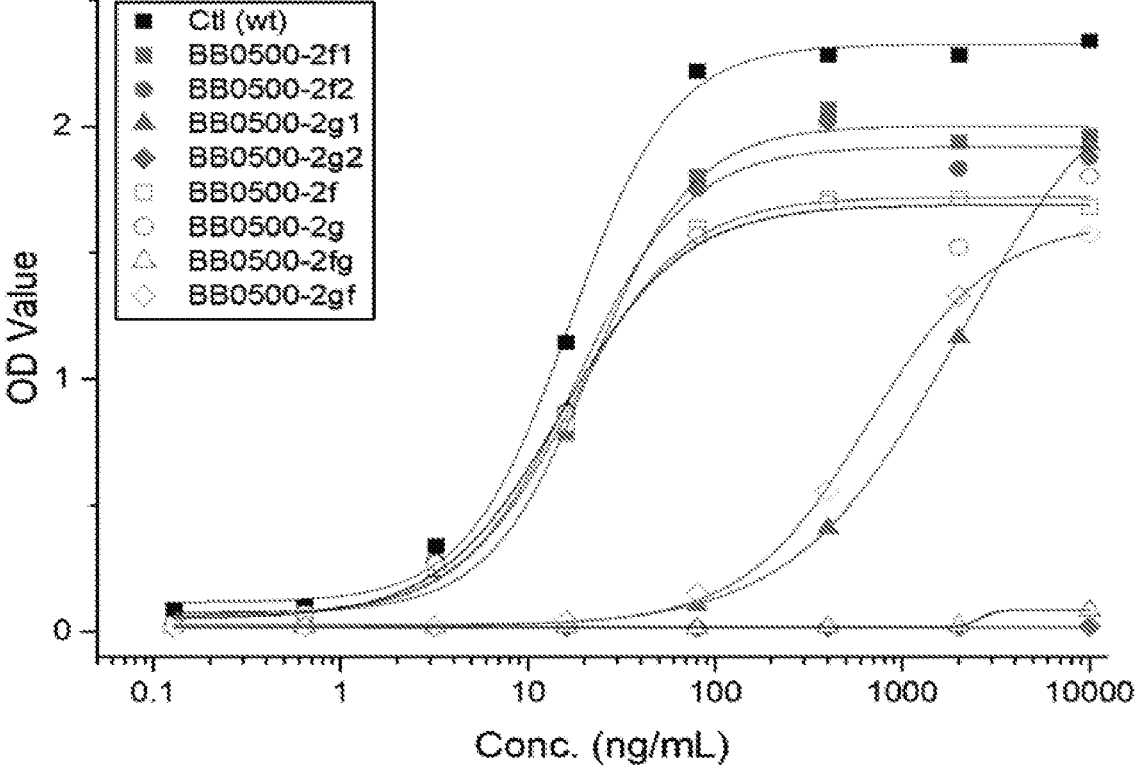
FIG. 3 shows binding curves of certain antibodies according to embodiments of the present invention, among other antibodies, to EGFR.

The results in FIG. 3 showed that mutant antibodies with single point alanine substitution at H2T59 (BB0500-2f1) or L2D50 (BB0500-2f2) had a small impact on $EC_{50}$ of EGFR binding activities. In contrast, the mutant antibody with single point alanine substitution at H3T103 (BB0500-2g1) had a huge impact on its EGFR binding activity ($EC_{50}$~100 fold change) and mutation at L1Y32 (BB0500-2g2) caused complete loss of EGFR binding activity. These results suggested that while H2T59 and L2D50 were minimally contributing to the overall target binding activity of Panitumumab, H3T103 and L1Y32 were either critically involved in the high-affinity association of Panitumumab/EGFR complex, or alanine substitutions at these places were detrimental to the proper conformation of the antigen binding surface. The upper plateau of the binding curves of neither BB0500-2f1 nor BB0500-2f2 reached to the level of wt control, suggesting that both substitutions impacted the off rate of the target binding kinetics.

Binding profiles of the double mutations revealed a much more complicated picture. First, BB0500-2f with alanine substitutions at both H2T59 and L2D50 did seem to have an additive effect, with minimal impact on EC50 yet an even lower upper plateau. Secondly, double alanine substitutions on H3T103/L2D50 (BB0500-2gf), or H2T59/L1Y32 (BB0500-2fg) behaved very similarly to that of single point mutation at either H3T103 or L1Y32 respectively (BB0500-2g1 or BB0500-2g2), suggesting that alanine substitution at either H3T103 or L1Y32 had a dominant effect on the overall binding activities of the mutant antibodies. Finally, and most surprisingly, double mutations at both H3T103 and L1Y32 (BB0500-2g) showed a decent binding activity, similar to that of H2T59 and L2D50 double mutations (BB0500-2f). This drastically rescued binding activities with double mutations suggested that, in addition to loss of side chain target interactions, each single mutation might induce conformation changes of H2 or L2 loop. The mutant H2 loop might collide with wt L2 loop and vice versa. In contrast the mutant H2 loop and mutant L2 loop might fit cohesively and as a result, mutant antibody with this particular pair of double mutations largely retained the overall EGFR binding activity.

Measurement of EGFR binging affinity of the mutant antibodies and control (wt) antibody to human EGFR is performed on Octet RED96e (Pall FortéBio). Affinity tests are performed in SD buffer (0.02% Tween-20, 0.1% BSA in PBS buffer, pH 7.4) using anti-human Fc Capture (AHC) biosensors. Antibody sample or buffer are dispensed into 96-well microtiter plates. AHC biosensors (Pall FortéBio) are pre-wet with SD buffer to establish a baseline before protein immobilization. The antibody sample is immobilized onto the biosensors. Binding association of the mutant antibodies or control (wt) antibody with EGFR is monitored, and subsequent disassociation in SD buffer is monitored. Mutant and control antibodies binding is evaluated at various concentrations of EGFR. Data are generated automatically by the Data Acquisition software, and data analysis is performed using FortéBio Data Analysis software.

The binding affinity data is presented in Table 2. The calculated $K_D$ of wt control antibody (Panitumumab) is $10^{-10}$M, and the $K_D$ of the mutants (BB0500-2f1, BB0500-2f2, BB0500-2n and BB0500-2g) had 10-100 folds reduction (in the range of $1\times10^{-9}$–$5\times10^{-8}$M), which is similar to the low affinity antibody BB05D3 (Nimotuzumab). The reductions were largely caused by faster dissociation rates with little changes in association rates. These data were in consistent with the ELISA data and support the hypothesis that the reduced saturation binding capacity of mutant antibodies was indeed cause by faster dissociation of the mutant antibody/target complex.

TABLE 2

| Results of Kinetic Binding Affinity Parameters to Mutant and wt Antibodies | | | |
| --- | --- | --- | --- |
| Samples | $k_{on}$ (1/Ms) | $k_{dis}$ (1/s) | $K_D$ (M) |
| Ctl (wt) | 6.33E+05 | 8.07E−05 | 1.27E−10 |
| BB05D3 | 1.04E+05 | 2.87E−03 | 2.77E−08 |

TABLE 2-continued

| | | | |
|---|---|---|---|
| Results of Kinetic Binding Affinity Parameters to Mutant and wt Antibodies | | | |
| Samples | $k_{on}$ (1/Ms) | $k_{dis}$ (1/s) | $K_D$ (M) |
| BB0500-2f1 | 6.55E+05 | 7.36E−04 | 1.12E−09 |
| BB0500-2f2 | 5.43E+05 | 1.54E-02 | 2.83E-08 |
| BB0500-2n | 5.43E+05 | 2.40E-02 | 4.41E-08 |
| BB0500-2g | 7.01E+05 | 2.72E-02 | 3.88E-08 |

3. Conjugation of Mutant Anti-EGFR Antibodies to Generate ADCs.

Under mild reduction conditions (TCEP: mAb=1-3, neutral pH, room temperature for <240 min), interchain disulfide bonds of an antibodies could be partially reduced and conjugated with drug-linker to form ADCs. To generated the drug conjugates, a purified antibody in phosphate buffer at neutral pH was added TCEP for partial reduction. Drug-linker (Mal-PEG$_2$-Val-Cit-PAB-eribulin or MC-Val-Cit-PAB-MMAE) in DMA was added and allowed to react with antibody to obtain desired drug-to-antibody ratio (DAR). To characterize the antibodies and ADCs, Hydrophobic Interaction Chromatography (HIC) was performed for the evaluation of drug distribution and molar ratio of drug and antibody in ADC. CE-SDS of non-reducing ADC was also performed to evaluate percentage of non-covalently linked components in the ADC product, like free light chains (L), free heavy chains (H), half antibodies (HL), intact antibodies (LHHL) and antibodies missing one or two light chains (HHL or HH).

Figure 4:
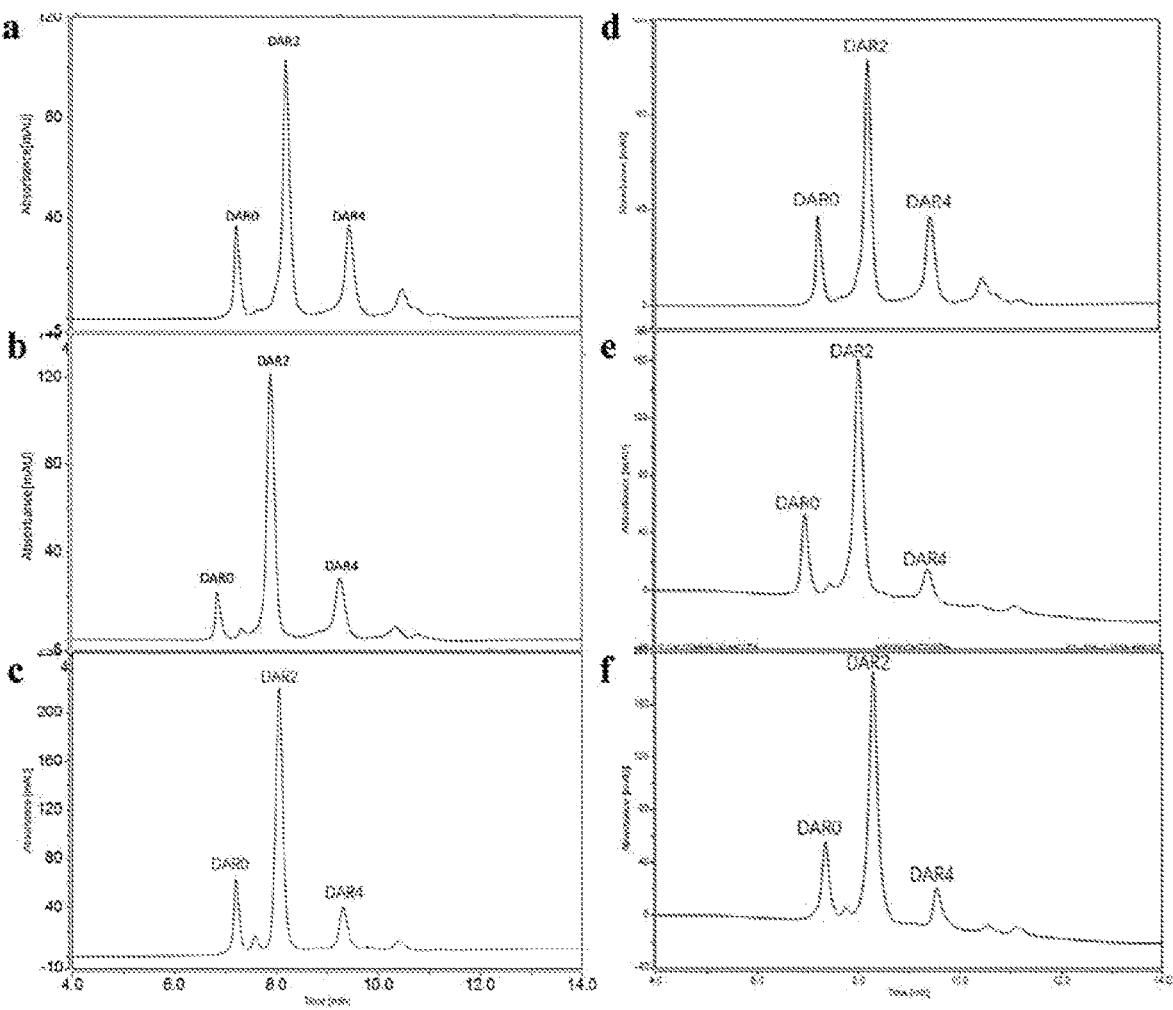
FIG. 4 shows HIC profiles of two ADCs made of certain antibodies according to embodiments of the present invention.

To make antibodies suitable for site specific drug conjugation, antibodies containing wt Panitumumab (and wt Nimotuzumab) variable sequences and alanine substitution sequences were made in a format containing special hinge sequences with an extra H—H inter chain disulfide bond upstream of the indigenous H—H double disulfide bond. The extra H—H disulfide bond was more vulnerable to reduction than the rest of the inter chain disulfide bonds. As a result, the cysteine residues forming this disulfide bond became preferred sites for drug conjugation as confirmed by LC-MS. The ADCs made of these engineered antibodies were predominantly made of DAR2 ADC species (FIG. 4a: BB0500-2f with eribulin, FIG. 4b: BB0500-2g with eribulin, FIG. 4c: BB0500-2n with eribulin; FIG. 4d: BB0500-2f with MMAE, FIG. 4e: BB0500-2g with MMAE, FIG. 4f: BB0500-2n with MMAE).

4. Cytotoxicity of ADCs made of Mutant Antibodies to EGFR High/Low-Expressing Cells.

To investigate the cytotoxicity of the mutant ADCs (BB0500-2f/2g/2n-eribulin, BB0500-2f/2g/2n-MMAE), in vitro cytotoxicity to target expressing cancer cells with varying EGFR expression levels was evaluated in comparison with low affinity ADC BB05D3-eribulin/MMAE (nimotuzumab ADC) and wild type Panitumumab ADC BB0500-2d-eribulin/MMAE (Ctl ADC) in a colorimetric-based cytotoxic assay. To perform the assay, target cells were seeded into a 96-well flat-bottom tissue culture plate at an optimized cell density for each cell line and incubated at 37° C., 5% CO2 overnight (16-20 hrs). Serial dilutions of ADC samples were transferred to cell plate and the assay plates were incubated for a defined period of time (3-5 days depend on cell lines) for optimal killing. Data analysis was performed using a dose response curve by four parameters logistic model.

Figure 5:
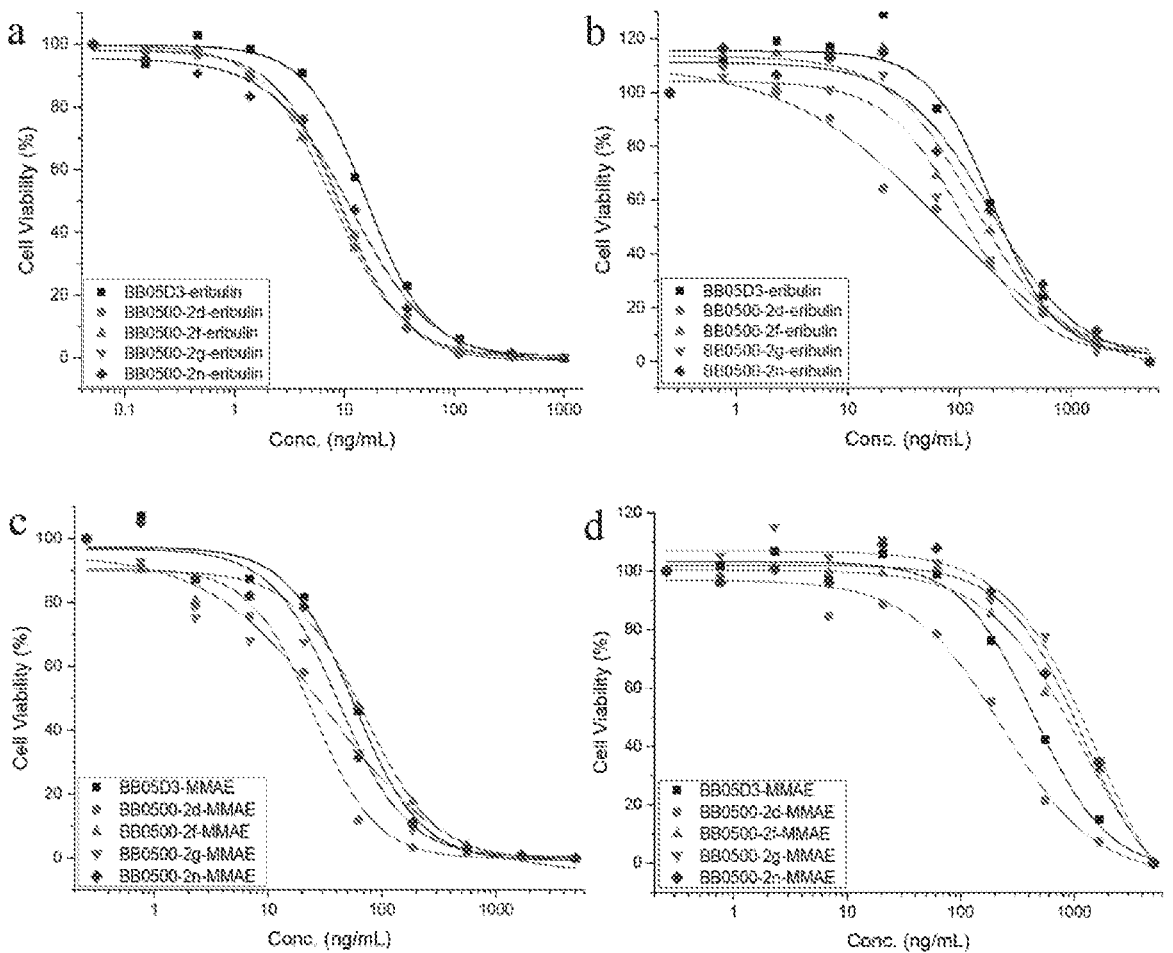
FIG. 5 shows cytotoxicity curves of certain ADCs according to embodiments of the present invention and comparative ADCs to EGFR-expressing cancer cells: (a) A431 cell, (b) NUGC3 cell, (c) A431 cell, (d) NUGC3 cell.

As shown in FIG. 5a/5b, ADCs made of three mutant antibodies (BB0500-2f, BB0500-2g and BB0500-2n) and a toxin eribulin exerted similarly potent cytotoxicity activities to EGFR high-expressing cells (A431 cells, FIG. 5a) as that of ADC made of antibody containing wt Panitumumab sequences (BB0500-2d-eribulin). All four ADCs were more potent to this EGFR high-expressing cells than the ADC made of the low affinity anti-EGFR antibody Nimotuzumab (BB05D3-eribulin). In contrast, to an EGFR low-expressing cell line (NUGC3 cells, FIG. 5b), the cytotoxic potency of the ADCs made from the three mutant antibodies (BB0500-2f/2g/2n) were closer to that of BB05D3-eribulin, while ADC made of antibody containing wt Panitumumab sequences was significantly more potent.

As shown in FIG. 5c/5d, ADCs made of three mutant antibodies (BB0500-2f, BB0500-2g and BB0500-2n) and a toxin MMAE exerted similarly potent cytotoxicity activities to EGFR high-expressing cell line (A431 cells, FIG. 5c) or EGFR low-expressing cell line (NUGC3 cells, FIG. 5d) as that of ADC made of the low affinity anti-EGFR antibody Nimotuzumab (BB05D3-eribulin). All four ADCs were less potent than the ADC made of antibody containing wt Panitumumab sequences (BB0500-2d-MMAE) to both EGFR high-expressing or low-expressing cells.

5. In Vivo Efficacy of ADCs Made of Mutant Antibodies to Tumor Xenografts

Figure 6:
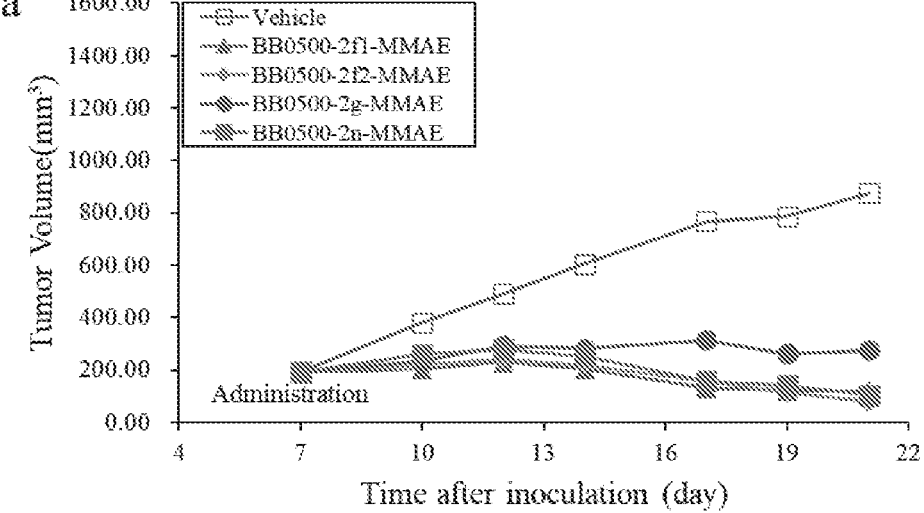
FIG. 6 shows changes of tumor volume over time in mice treated with certain example ADCs of the present disclosure as compared to the tumor volume in mice treated with vehicle.
Figure 6:
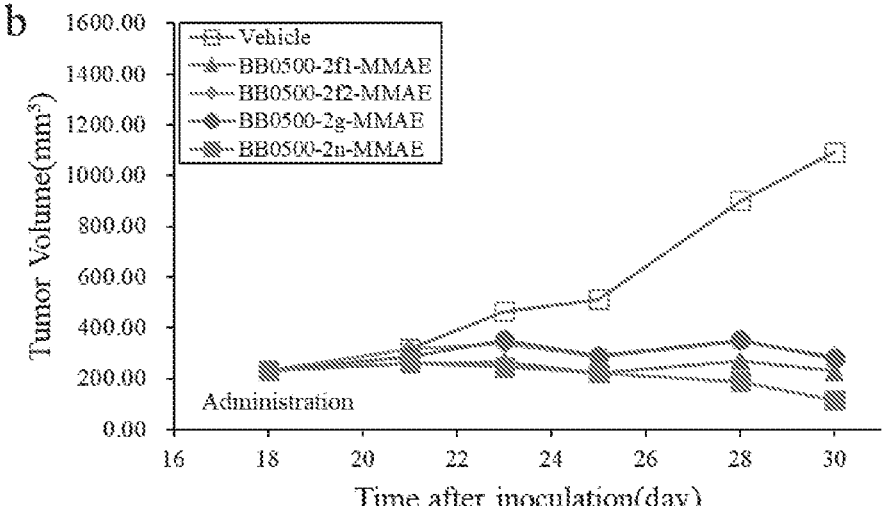

The antitumor activities of ADCs made of mutant antibodies and MMAE were assessed in epidermoid carcinoma and lung cancer xenograft models established in nude mice. A431 (epidermoid carcinoma) and NCI-H441 (lung cancer) cells were implanted in the back of athymic nude mice. Tumor-bearing mice were treated with vehicle (control) or 5 mg/kg ADCs (BB0500-2f1-MMAE, BB0500-2f2-MMAE, BB0500-2g-MMAE, BB0500-2n-MMAE) once. Tumor volume was measured at various time points after administration. The results are shown in FIG. 6, the tumor volume in mice treated with ADCs made of mutant antibodies decreased in A431 xenograft model (FIG. 6a) and NCI-H441 xenograft model (FIG. 6b) as compared to the tumor volume in mice treated with vehicle.

While specific embodiments of the present invention have been described in detail, those skilled in the art will understand that various modifications and substitutions can be made to those details according to all teachings that have been disclosed, and all of these changes fall within the scope of the present invention. The full scope of the invention is given by the appended claims and any equivalents thereof.

REFERENCES

[1]. Roy S. Herbst, M.D., Ph.D. *Int. J. Radiation Oncology Biol. Phys.* 2004;59:21-26.

[2]. Hongtao Zhang, Alan Berezov, Qiang Wang,et al. *The Journal of Clinical Investigation.* 2007; 117: 2051-2058.

[3]. Shailaja Kalyankrishn, Jennifer R. Grandis., et al. *Journal of Clinical Oncology.* 2006; 4:2666-2672.

[4]. Hina S. Rehmani Natalia Issaeva, et al. *Ann Transl Med.* 2020; 8:813.

[5]. Gillian Bethune, Drew Bethune, Neale Ridgway. et al. *J Thorac Dis.*2010; 2: 48-51.

[6]. Fadi S. Saadeh, Rami Mahfouz, Hazem I. Assi, et al. *The International Journal of Biological Markers.* 2018; 33: 22-32.

[7]. Torsten O. Nielsen, Forrest D. Hsu, Kristin Jensen, et al. *Clinical Cancer Research.* 2004; 10:5367-5374.

[8]. Katsuya Nakai, Mien-Chie Hung, Hirohito Yamaguchi. et al. *Am J Cancer Res* 2016; 6:1609-1623.

[9]. Diaz-Serrano, A., Gella, P., Jiménez, E., et al. *Drugs.* 2018;78: 893-911.

[10]. Emily Padfield, Hayley P. Ellis, Kathreena M. Kurian., et al. *Frontiers in Oncology.* 2015; 5:1-8.

[11]. Yuanhong Xie, Yingxuan Chen, Jingyuan Fang, et al. *Signal Transduction and Targeted Therapy.* 2020; 5:22.

[12]. E. Martinelli, R. De Palma, M. Orditura et al.*Clinical and Experimental Immunology.* 2009; 158: 1-9.

[13]. Wenqi Cai, Lisi Zeng, Lifeng Wang. et al. *Frontiers in Oncology.* 2020; 10:1-16.

[14]. Melarkode S. Ramakrishnan, Anand Eswaraiah, Tania Crombet, et al. *mAbs,* 2009; 1:41-48.

All patents and non-patent literature references described herein are incorporated by reference herein in their entireties.

While the invention has been described above in connection with one or more embodiments, it should be understood that the invention is not limited to those embodiments, and the description is intended to cover all alternatives, modifications, and equivalents, as may be included within the spirit and scope of the appended claims.

```
Sequence Listing
(VH of BB0500-2f1, BB0500-2f, BB0500-2n
and BB0500-2fg)
                              SEQ ID NO: 1
QVQLQESGPGLVKPSETLSLTCTVSGGSVSSGDYYWTWIR

QSPGKGLEWIGHIYYSGNANYNPSLKSRLTISIDTSKTQF

SLKLSSVTAADTAIYYCVRDRVTGAFDIWGQGTMVTVSS (VL of BB0500-2f1 and BB0500-2g1)
                              SEQ ID NO: 2
DIQMTQSPSSLSASVGDRVTITCQASQDISNYLNWYQQKP

GKAPKLLIYDASNLETGVPSRFSGSGSGTDFTFTISSLQP

EDIATYFCQHFDHLPLAFGGGTKVEIK (VH of BB0500-2f2 and BB0500-2g2)
                              SEQ ID NO: 3
QVQLQESGPGLVKPSETLSLTCTVSGGSVSSGDYYWTWIR

QSPGKGLEWIGHIYYSGNTNYNPSLKSRLTISIDTSKTQF

SLKLSSVTAADTAIYYCVRDRVTGAFDIWGQGTMVTVSS (VL of BB0500-2f2, BB0500-2f, BB0500-2n
and BB0500-2gf)
                              SEQ ID NO: 4
DIQMTQSPSSLSASVGDRVTITCQASQDISNYLNWYQQKP

GKAPKLLIYAASNLETGVPSRFSGSGSGTDFTFTISSLQP

EDIATYFCQHFDHLPLAFGGGTKVEIK (VH of BB0500-2g1, BB0500-2g,
and BB0500-2gf)
                              SEQ ID NO: 5
QVQLQESGPGLVKPSETLSLTCTVSGGSVSSGDYYWTWIR

QSPGKGLEWIGHIYYSGNTNYNPSLKSRLTISIDTSKTQF

SLKLSSVTAADTAIYYCVRDRVAGAFDIWGQGTMVTVSS (VL of BB0500-2g2, BB0500-2g,
and BB0500-2fg)
                              SEQ ID NO: 6
DIQMTQSPSSLSASVGDRVTITCQASQDISNALNWYQQKP

GKAPKLLIYDASNLETGVPSRFSGSGSGTDFTFTISSLQP

EDIATYFCQHFDHLPLAFGGGTKVEIK
```

```
                    -continued
(BB0500-2f1/2f/2fg heavy chain)
                              SEQ ID NO: 7
QVQLQESGPGLVKPSETLSLTCTVSGGSVSSGDYYWTWIR

QSPGKGLEWIGHIYYSGNANYNPSLKSRLTISIDTSKTQF

SLKLSSVTAADTAIYYCVRDRVTGAFDIWGQGTMVTVSSA

STKGPSVFPLAPCSRSTSESTAALGCLVKDYFPEPVTVSW

NSGALTSGVHTFPAVLQSSGLYSLSSVVTVPSSNFGTQTY

TCNVDHKPSNTKVDKTVEPKSDKCTHTVECPPCPAPPVAG

PSVFLFPPKPKDTLMISRTPEVTCVVVDVSHEDPEVQFNW

YVDGVEVHNAKTKPREEQFNSTFRVVSVLTVVHQDWLNGK

EYKCKVSNKGLPAPIEKTISKTKGQPREPQVYTLPPSREE

MTKNQVSLTCLVKGFYPSDISVEWESNGQPENNYKTTPPM

LDSDGSFFLYSKLTVDKSRWQQGNVFSCSVMHEALHNHYT

QKSLSLSPGK (BB0500-2f1/2g1 light chain)
                              SEQ ID NO: 8
DIQMTQSPSSLSASVGDRVTITCQASQDISNYLNWYQQKP

GKAPKLLIYDASNLETGVPSRFSGSGSGTDFTFTISSLQP

EDIATYFCQHFDHLPLAFGGGTKVEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC (BB0500-2f2/2g2 heavy chain)
                              SEQ ID NO: 9
QVQLQESGPGLVKPSETLSLTCTVSGGSVSSGDYYWTWIR

QSPGKGLEWIGHIYYSGNTNYNPSLKSRLTISIDTSKTQF

SLKLSSVTAADTAIYYCVRDRVTGAFDIWGQGTMVTVSSA

STKGPSVFPLAPCSRSTSESTAALGCLVKDYFPEPVTVSW

NSGALTSGVHTFPAVLQSSGLYSLSSVVTVPSSNFGTQTY

TCNVDHKPSNTKVDKTVEPKSDCKTHTVECPPCPAPELLG

GPSVFLFPPKPKDTLMISRTPEVTCVVVDVSHEDPEVKFN

WYVDGVEVHNAKTKPREEQYNSTYRVVSVLTVLHQDWLNG

KEYKCKVSNKALPAPIEKTISKAKGQPREPQVYTLPPSRE

EMTKNQVSLTCLVKGFYPSDIAVEWESNGQPENNYKTTPP

VLDSDGSFFLYSKLTVDKSRWQQGNVFSCSVMHEALHNHY

TQKSLSLSPGK (BB0500-2f2/2f/2gf/2n light chain)
                              SEQ ID NO: 10
DIQMTQSPSSLSASVGDRVTITCQASQDISNYLNWYQQKP

GKAPKLLIYAASNLETGVPSRFSGSGSGTDFTFTISSLQP

EDIATYFCQHFDHLPLAFGGGTKVEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC
```

-continued (BB0500-2g1/2g/2gf heavy chain)
SEQ ID NO: 11

QVQLQESGPGLVKPSETLSLTCTVSGGSVSSGDYYWTWIR

QSPGKGLEWIGHIYYSGNTNYNPSLKSRLTISIDTSKTQF

SLKLSSVTAADTAIYYCVRDRVAGAFDIWGQGTMVTVSSA

STKGPSVFPLAPCSRSTSESTAALGCLVKDYFPEPVTVSW

NSGALTSGVHTFPAVLQSSGLYSLSSVVTVPSSNFGTQTY

TCNVDHKPSNTKVDKTVEPPKSCDKTHTVECPPCPAPPVA

GPSVFLFPPKPKDTLMISRTPEVTCVVVDVSHEDPEVQFN

WYVDGVEVHNAKTKPREEQFNSTFRVVSVLTVVHQDWLNG

KEYKCKVSNKGLPAPIEKTISKTKGQPREPQVYTLPPSRE

EMTKNQVSLTCLVKGFYPSDISVEWESNGQPENNYKTTPP

MLDSDGSFFLYSKLTVDKSRWQQGNVFSCSVMHEALHNHY

TQKSLSLSPGK (BB0500-2g2/2g/2fg light chain)
SEQ ID NO: 12

DIQMTQSPSSLSASVGDRVTITCQASQDISNALNWYQQKP

GKAPKLLIYDASNLETGVPSRFSGSGSGTDFTFTISSLQP

EDIATYFCQHFDHLPLAFGGGTKVEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC (BB0500-2n heavy chain)
SEQ ID NO: 13

QVQLQESGPGLVKPSETLSLTCTVSGGSVSSGDYYWTWIR

QSPGKGLEWIGHIYYSGNANYNPSLKSRLTISIDTSKTQF

SLKLSSVTAADTAIYYCVRDRVTGAFDIWGQGTMVTVSSA

STKGPSVFPLAPCSRSTSESTAALGCLVKDYFPEPVTVSW

NSGALTSGVHTFPAVLQSSGLYSLSSVVTVPSSNFGTQTY

TCNVDHKPSNTKVDKTVEPPKSDCKTHTVECPPCPAPEAA

GGPSVFLFPPKPKDTLMISRTPEVTCVVVDVSHEDPEVKF

NWYVDGVEVHNAKTKPREEQYNSTYRVVSVLTVLHQDWLN

-continued

GKEYKCKVSNKALPAPIEKTISKAKGQPREPQVYTLPPSR

EEMTKNQVSLTCLVKGFYPSDIAVEWESNGQPENNYKTTP

PVLDSDGSFFLYSKLTVDKSRWQQGNVFSCSVMHEALHNH

YTQKSLSLSPGK (VH CDR1 of BB0500-2f1/2f2/2g1/2g2/
2f/2g/2fg/2gf/2n, wt)
SEQ ID NO: 14

GGSVSSGDY (VH CDR2 of BB0500-2f/2f1/2fg/2n,
with T59A mutation)
SEQ ID NO: 15

YYSGNA (VH CDR2 of BB0500-2f2/2g1/2g2/
2g/2gf, wt)
SEQ ID NO: 16

YYSGNT (VH CDR3 of BB0500-2g/2g1/2gf,
with T103A mutation)
SEQ ID NO: 17

DRVAGAFDI (VH CDR3 of BB0500-2f1/2f2/2g2/2f/
2fg/2n, wt)
SEQ ID NO: 18

DRVTGAFDI (VL CDR1 of BB0500-2g2/2g/2fg,
with Y32A mutation)
SEQ ID NO: 19

QASQDISNALN (VL CDR1 of BB0500-2f1/2f2/2g1/
2f/2gf/2n, wt)
SEQ ID NO: 20

QASQDISNYLN (VL CDR2 of BB0500-2f2/2f/2gf/2n,
with D50A mutation)
SEQ ID NO: 21

AASNLET (VL CDR2 of BB0500-2f1/2g1/2g2/
2g/2fg, wt)
SEQ ID NO: 22

DASNLET (VL CDR3 of BB0500-2f1/2f2/2g1/2g2/
2f/2g/2fg/2gf/2n, wt)
SEQ ID NO: 23

QHFDHLPLA

---

The invention claimed is:

1. An isolated antibody comprising:

(a1) a heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b1) a light chain variable domain comprising a CDR1 region, a CDR2 region, and a CDR3 region comprising the amino acid sequences of SEQ ID NO: 20, SEQ ID NO: 21, and SEQ ID NO: 23, respectively; or (a2) a heavy chain variable domain comprising a CDR1 region, a CDR2 region, and a CDR3 region comprising the amino acid sequences of SEQ ID NO: 14, SEQ ID NO: 16, and SEQ ID NO: 17, respectively, and (b2) a light chain variable domain comprising a CDR1 region, a CDR2 region, and a CDR3 region comprising the amino acid sequences of SEQ ID NO: 19, SEQ ID NO: 22, and SEQ ID NO: 23, respectively; or (a3) a heavy chain variable domain comprising a CDR1 region, a CDR2 region, and a CDR3 region comprising the amino acid sequences of SEQ ID NO: 14, SEQ ID NO: 15, and SEQ ID NO: 18, respectively, and (b3) a light chain variable domain comprising a CDR1 region, a CDR2 region, and a CDR3 region comprising the amino acid sequences of SEQ ID NO: 20, SEQ ID NO: 22, and SEQ ID NO: 23, respectively;

(a4) a heavy chain variable domain comprising a CDR1 region, a CDR2 region, and a CDR3 region comprising the amino acid sequences of SEQ ID NO: 14, SEQ ID NO: 16, and SEQ ID NO: 18, respectively, and (b4) a light chain variable domain comprising a CDR1 region, a CDR2 region, and a CDR3 region comprising the amino acid sequences of SEQ ID NO: 20, SEQ ID NO: 21, and SEQ ID NO: 23, respectively;

wherein the isolated antibody specifically binds with human EGFR protein.

2. An isolated antibody comprising:

(a) a heavy chain having a variable domain comprising the amino acid sequence of SEQ ID NO: 1, and a light chain having a variable domain comprising the amino acid sequence of SEQ ID NO: 4; or (b) a heavy chain having a variable domain comprising the amino acid sequence of SEQ ID NO: 5, and a light chain having a variable domain comprising the amino acid sequence of SEQ ID NO: 6; or (c) a heavy chain having a variable domain comprising the amino acid sequence of SEQ ID NO: 1, and a light chain having a variable domain comprising the amino acid sequence of SEQ ID NO: 2; or (d) a heavy chain having a variable domain comprising the amino acid sequence of SEQ ID NO: 3, and a light chain having a variable domain comprising the amino acid sequence of SEQ ID NO: 4.

3. The isolated antibody of claim 2, wherein the antibody comprises: a heavy chain having a variable domain comprising the amino acid sequence of SEQ ID NO: 1, and a light chain having a variable domain comprising the amino acid sequence of SEQ ID NO: 4.

4. An isolated antibody comprising:

(a) a heavy chain comprising the amino acid sequence of SEQ ID NO: 7, and a light chain comprising the amino acid sequence of SEQ ID NO: 10; or (b) a heavy chain comprising the amino acid sequence of SEQ ID NO: 13, and a light chain comprising the amino acid sequence of SEQ ID NO: 10; or (c) a heavy chain comprising the amino acid sequence of SEQ TD NO: 11, and a light chain comprising the amino acid sequence of SEQ ID NO: 12; or (d) a heavy chain comprising the amino acid sequence of SEQ ID NO: 7, and a light chain comprising the amino acid sequence of SEQ ID NO: 8; or (e) a heavy chain comprising the amino acid sequence of SEQ ID NO: 9, and a light chain comprising the amino acid sequence of SEQ ID NO: 10.

5. The isolated antibody of claim 3, wherein the antibody comprises: a heavy chain comprising the amino acid sequence of SEQ ID NO: 7, and a light chain comprising the amino acid sequence of SEQ ID NO: 10.

6. The isolated antibody of any of claims 1-5, wherein the antibody is a monoclonal antibody.

7. A nucleic acid molecule encoding the antibody of any one of claims 1-5.

8. An expression vector containing the nucleic acid molecule of claim 7.

9. A host cell containing the expression vector of claim 8.

10. An antibody-drug conjugate (ADC) or a pharmaceutically acceptable salt thereof, comprising: the antibody of claim 1 conjugated to a cytotoxic drug by a chemical linker.

11. The ADC or the pharmaceutically acceptable salt thereof, of claim 10, wherein the cytotoxic drug is selected from the group consisting of eribulin, monomethyl auristatin E (MMAE), monomethyl auristatin F (MMAF), auristatin E, auristatin F, maytansine DM1, maytansine DM4, maytansinol, sandramycin, pyrrolobenzodiazepine, pyrrolobenzodiazepine dimer, anthracyclines, calicheamicin, dolastatin 10, duocarmycin, cloxorubicin, thailanstatin A, uncialamycin, amanitins, ricin, diphtheria toxin, ml, interleukins, tumor necrosis factors, chemokines, irinotecan, exatecan, and nanoparticles.

12. The ADC or the pharmaceutically acceptable salt thereof, of claim 10, wherein the chemical linker comprises a portion that is selected from the group consisting of 6-maleimidocaproyl (MC), maleimidopropionyl (MP), valine-citrulline (Val-Cit), alanine-phenylalanine (ala-phe), p-aminobenzyloxycarbonyl (PAB), 6-maleimidocaproyl-Val-Cit-p-aminobenzyloxycarbonyl (MC-Val-Cit-PAB), Mal-PEG$_n$-Val-Cit-PAB (n=1-20), Phe-Lys(Fmoc)-PAB, Aloc-D-Ala-Phe-Lys(Aloc)-PAB-PNP, Boc-Phe-(Alloc) Lys-PAB-PNP, and perfluorophenyl 3-(pyridine-2-yldisulfanyl) propanoate.

13. The ADC or the pharmaceutically acceptable salt thereof, of claim 10, wherein the cytotoxic drug is eribulin.

14. The ADC or the pharmaceutically acceptable salt thereof, of claim 13, wherein the antibody comprises: a heavy chain having a variable domain comprising the amino acid sequence of SEQ ID NO: 1, and a light chain having a variable domain comprising the amino acid sequence of SEQ ID NO: 4.

15. The ADC or the pharmaceutically acceptable salt thereof, of claim 10, wherein the cytotoxic drug is MMAE.

16. The ADC or the pharmaceutically acceptable salt thereof, of claim 15, wherein the antibody comprises: a heavy chain having a variable domain comprising the amino acid sequence of SEQ ID NO: 1, and a light chain having a variable domain comprising the amino acid sequence of SEQ ID NO: 4.

17. A pharmaceutical composition comprising:

(a) the antibody of claim 1, or the ADC or a pharmaceutically acceptable salt thereof, of claim 10, and (b) a pharmaceutically acceptable carrier.

18. A method of treating cancer in a human subject, comprising administering to the subject a therapeutically effective amount of the pharmaceutical composition of claim 17.

19. The method of claim 18, wherein the cancer is selected from the group consisting of: non-small cell lung cancer, epidermoid carcinoma, breast cancer, colorectal cancer, ovarian cancer, cervical cancer, bladder cancer, oesophageal cancer, head and neck cancers, glioblastoma and nasopharyngeal cancer.

* * * * *